United States Patent [19]

Kynor

[11] Patent Number: 5,311,867
[45] Date of Patent: May 17, 1994

[54] DETECTION AND GROUPING ANALYSIS OF CARDIAC CYCLES

[75] Inventor: David Kynor, San Diego, Calif.

[73] Assignee: Biomagnetic Technologies, Inc., San Diego, Calif.

[21] Appl. No.: 141

[22] Filed: Jan. 4, 1993

[51] Int. Cl.$^5$ .............................................. A61B 5/02
[52] U.S. Cl. ................... 128/653.1; 128/695
[58] Field of Search ............... 128/653.1, 695, 696, 128/702; 364/413.06; 324/244, 248

[56] References Cited

U.S. PATENT DOCUMENTS

| | | | |
|---|---|---|---|
| 4,079,730 | 3/1978 | Wikswo, Jr. et al. | 128/653.1 |
| 5,136,242 | 8/1992 | Abraham-Fuchs | 128/653.1 |
| 5,215,098 | 6/1993 | Steinhaus et al. | 128/702 |

Primary Examiner—William E. Kamm
Assistant Examiner—George Manuel
Attorney, Agent, or Firm—Gregory Garmong

[57] ABSTRACT

The physiology of the heart is analyzed by measuring a series of cardiac cycles using a biomagnetometer or other device capable of detecting cardiac cycles, classifying the cardiac cycles into groups according to the degree of correlation with a template cardiac cycle for the group, and associating the cardiac cycles of the groups with an origin location within the subject. The classifying operation preferably includes selecting a template cardiac cycle against which other previously ungrouped cardiac cycles are to be correlated, performing a correlation analysis of all previously ungrouped cardiac cycles with the template cardiac cycle, and associating with the template cardiac cycle all previously ungrouped cardiac cycles having at least a preselected degree of correlation, to form a group.

18 Claims, 2 Drawing Sheets

DETECTION AND GROUPING ANALYSIS OF CARDIAC CYCLES

BACKGROUND OF THE INVENTION

This invention relates to the measurement of the functioning of the heart, and, more particularly, to the analysis of cardiac cycle signals.

The heart is a muscle that operates in response to a variety of electrical signals originating both inside and outside the heart. The electrical signals may be monitored and displayed, producing a continuing series of signals familiar to most persons as an electrocardiogram (ECG). These cardiac cycle signals can, in turn, be used to assess the health of the heart and the presence of some types of heart problems.

The analysis and understanding of the signals produced by the heart, and their relation to the health of the heart, is hampered by several circumstances. The electrical signal contains a great deal of information, since the heart beats about once each second. If each period of one second produced identical electrical signals, the analysis of the cardiac cycles would be straightforward. However, that is not the case, and there is typically quite a bit of variation in the heart electrical signal with time. There may be highly regular signals, occasional but still regular signals, and anomalous, nearly one-of-a-kind signals. The measured electrical signal of the heart is therefore in fact a mixture of signals produced in a variety of ways.

Further, the various types of signals may originate in different parts of the heart. As an example, a highly regular electrical signal may originate in one part of the heart. Some electrical signals may originate elsewhere, and may not interfere with the normal production of the regular signals. However, yet other signals, originating in yet other regions of the heart, may interrupt the normal operation of the heart and lead to dysfunctions such as lethal arrhythmias. The understanding of the functioning of the heart in health and in sickness may lie in determining the temporal and spatial relationships of various electrical signals to each other.

Most studies of the heart and its electrical signals have been performed by electrocardiography. Electrical pickup sensors are attached to the surface of the body. The electrical signals produced during the functioning of the heart are detected and recorded, and are available for more detailed studies at a later time. The electrocardiogram has the disadvantage that it cannot readily determine the precise physical location of the origin of the signals.

There is therefore a need for an improved approach to the study of the heart in which both the time series and physical origin of electrical signals can be measured. It is also necessary to identify the information of value from the mass of electrical signal information, and to use that information in the temporal and spatial analyses. The present invention provides a necessary advance in the art toward fulfilling this need, and further provides related advantages.

SUMMARY OF THE INVENTION

The present invention provides an apparatus and method for analyzing the electrical character of the functioning of the heart. The output signals of the heart are measured in a time series, in a manner such that the location of the origin of each signal can be determined. The mammoth stream of data is reduced to a meaningful form, from which common types of features can be associated together. As a result, anomalous features of the cardiac cycle can be identified. Particular events such as ectopic beats associated with events such as premature ventricular contractions can be identified without the need for detailed visual examination of the entire data set. In some instances, the physical origin of each type of feature of the output signal can be related to the origin of other signals. This approach can therefore provide to those studying the heart an aid for understanding the temporal and spatial interrelationships of features of the cardiac cycle, so that such persons can investigate the various states of normal and abnormal functioning.

In accordance with the invention, apparatus for measuring the physiology of the heart comprises means for detecting cardiac cycles of a subject (such as a biomagnetometer or electrocardiograph), means for storing the patterns of a series of cardiac cycles detected by the means for detecting, means for performing correlation analysis of cardiac cycles in the series of cardiac cycles, and means for classifying groupings of cardiac cycles. The means for classifying includes means for identifying a first template cardiac cycle and means for forming a first selected group of cardiac cycles from among those of the series of cardiac cycles having at least a first preselected degree of correlation with the first template cardiac cycle, and leaving a first ungrouped group of cardiac cycles having a correlation less than the first preselected degree of correlation. The means for classifying further includes means for selecting a second template cardiac cycle from the first ungrouped group of cardiac cycles, and means for forming a second group of cardiac cycles from among the first ungrouped group of cardiac cycles having at least a second preselected degree of correlation with the second template cardiac cycle, and leaving a second ungrouped group of cardiac cycles having a correlation less than the second preselected degree of correlation.

The apparatus desirably includes means for averaging all of the cardiac cycles within a group on a point-by-point basis, to yield an average cardiac cycle that is statistically smoothed. This averaged cardiac cycle may then be associated with a physical condition of the subject's body in some cases. The averaged cardiac cycle, its relative frequency, and its relation to other features of the cardiac cycle, as well as its origin, can be displayed for a person studying the heart of the subject. This approach, as applied to the analysis of all of the groups of cardiac cycles, can lead to an understanding of the role of each of the types of cardiac cycles in normal and abnormal heart functioning.

Further in accordance with the invention, a method for measuring the physiology of the heart comprises the steps of providing an apparatus that detects cardiac cycles of a subject, detecting magnetic signals corresponding to a time sequence of a plurality of cardiac cycles of a subject utilizing the biomagnetometer, and classifying the series of cardiac cycles into a number of groups according to the degree of correlation of each cardiac cycle with a template cardiac cycle for each group.

Preferably, the step of classifying includes the substeps of selecting a template cardiac cycle against which other previously ungrouped cardiac cycles are to be correlated, performing a correlation analysis of all previously ungrouped cardiac cycles with the template cardiac cycle, and associating with the template cardiac cycle all previously ungrouped cardiac cycles having at least a preselected degree of correlation, to form a group. The template cardiac cycle for each group correlation is preferably the previously ungrouped cardiac cycle having the lowest degree of correlation with the prior template cardiac cycle.

The present invention provides an apparatus and method for analyzing the electrical output signals of the heart. It permits the reduction and understanding of large amounts of data, so that the investigator can make correlations of various phenomena. Other features and advantages of the invention will be apparent from the following more detailed description of the preferred embodiment, taken in conjunction with the accompanying drawings which illustrate, by way of example, the principles of the invention.

DETAILED DESCRIPTION OF THE INVENTION

Figure 1:
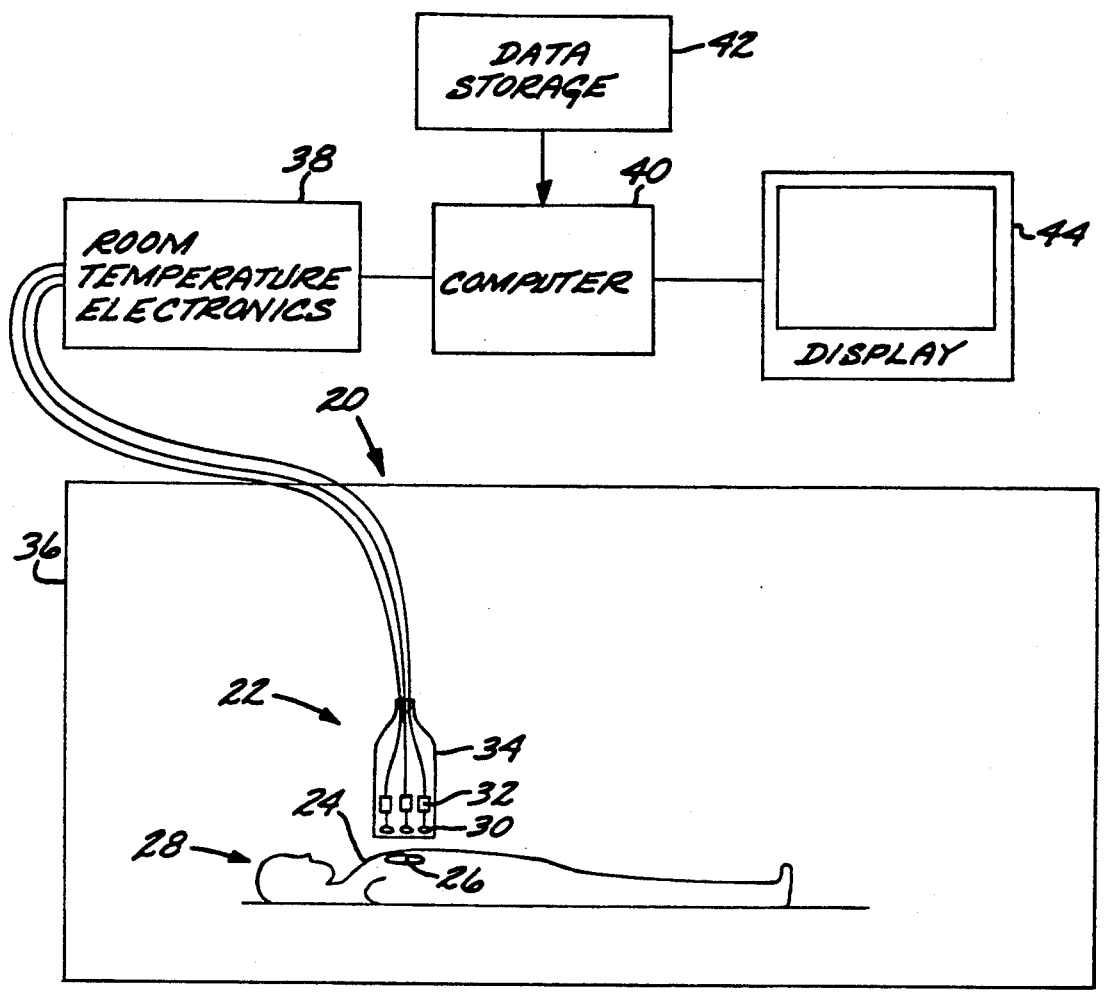
FIG. 1 is a schematic view of a preferred apparatus for analyzing the cardiac cycle of a subject.
Figure 3:
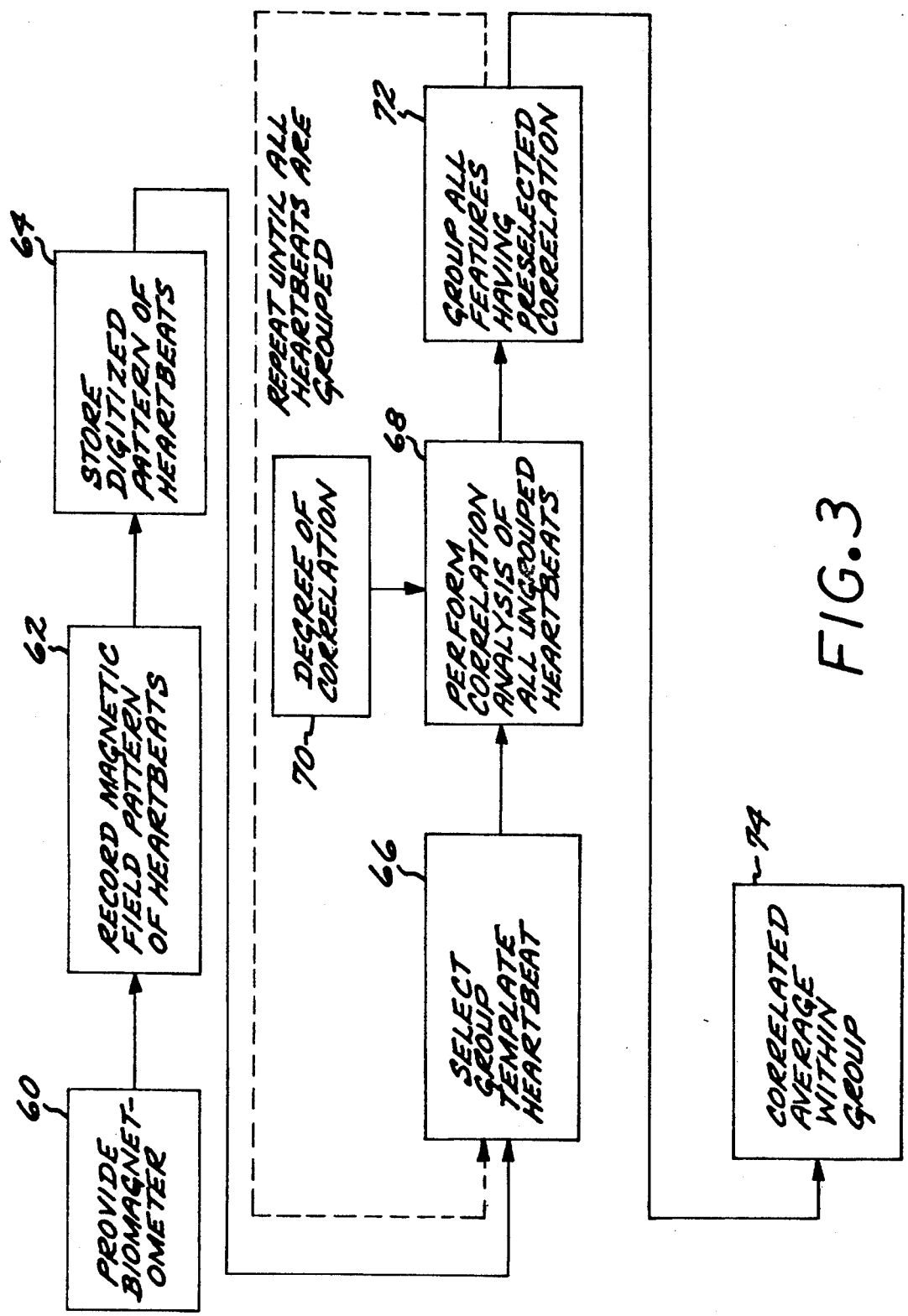
FIG. 3 is a flowchart for the method of the invention.

FIG. 1 depicts a preferred apparatus 20 according to the present invention, and FIG. 3 illustrates the preferred method for practicing the invention. Referring to FIG. 1, the apparatus 20 utilizes a biomagnetometer 22 to detect magnetic fields produced by electric currents flowing within the body 24, and specifically the heart 26, of a subject 28. The biomagnetometer 22 includes at least one, and preferably a plurality of magnetic field pickup coils 30 that produce a small electric current responsive to a magnetic field flux. Each pickup coil 30 delivers its current to a sensitive magnetic field detector, preferably a superconducting quantum interference device ("SQUID") 32. The SQUID 32 and the pickup coil 30 are normally operated at a cryogenic temperature to attain maximum sensitivity. A cryogenic dewar 34 encloses the SQUID 32 and pickup coil 30 and provides such a cryogenic environment.

The subject 28, pickup coils 30, SQUIDs 32, and dewar 34 may be located inside a magnetically shielded room 36 to minimize the effects of any external magnetic fields that might otherwise be detected and erroneously thought to be produced by the heart. The signals of the SQUIDs 32 are conducted to the exterior of the magnetically shielded room 36 to room-temperature electronics 38 that amplifies and conditions the signals. The conditioned signals are supplied to a computer 40, which may do real-time signal processing on the data, or store the information in a mass storage device 42 for later analysis. After the signals have been processed in the manner to be discussed in conjunction with FIG. 3, the results are presented on a display 44.

Biomagnetometers and related structure are known in the art and are available commercially from companies such as Biomagnetic Technologies, Inc., San Diego, Calif. Biomagnetometers and their components are shown in U.S. Pat. Nos. 4,793,355; 4,773,952; 5,061,680; and 5,158,932. The operation of SQUID systems and their electronics are shown in U.S. Pat. Nos. 3,980,076; 4,079,730; 4,386,361; and 4,403,189. A magnetically shielded room is shown in U.S. Pat. No. 3,557,777. The disclosures of all of these patents are incorporated by reference.

This depicted approach is preferred, but other, less sensitive magnetic field detection approaches may be used, if desired. The detection of the magnetic field of the heart does not require as much sensitivity as does the detection of magnetic fields of the brain.

The cardiac cycle information may also be gathered by other techniques, such as electrocardiography (ECG). If so, conventional electrocardiographic sensors are used to gather cardiac cycle data. That data is stored in the computer 40 and analyzed as will be discussed subsequently.

Figure 2:
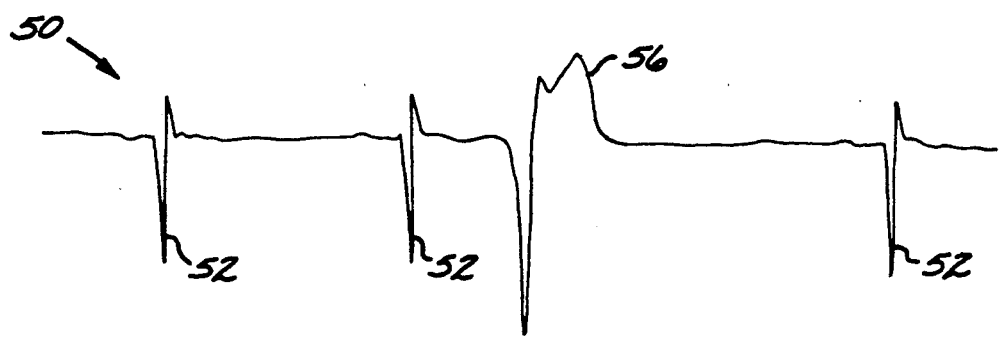
FIG. 2 is an idealized magnetic field signal produced by a heart.

FIG. 2 is an idealized version of a cardiac cycle pattern 50 that would be read and stored by the computer 40 in a digitized format. In this idealized pattern 50, there are three types of cardiac cycle. (As used herein, a "cardiac cycle" is a feature of the pattern 50. It may be, but is not necessarily, associated on a one-to-one basis with the signal that might be detected in a stethoscope, for example, inasmuch as the actual electrical and magnetic pattern of the heart is much more complex than the "heartbeat" detected with a stethoscope.) One type of cardiac cycle 52 is shown as regular and repeating, or it may be a A group may have many members, signifying that the cardiac cycle type occurs frequently. A group may have fewer members, indicating that its members occur regularly but less often. A group may have only one or a few members, indicating that the group represents some spurious signal or a physiologically significant but anomalous cardiac cycle. The cardiac cycles of the pattern are classified into respective groups by an iterative process depicted in elements 66, 68, 70, and 72, which is repeated until all cardiac cycles of the pattern have been assigned into a group.

To perform a group classification, a group template is first selected, numeral 66. In forming the first group, the template is selected at random from all members of the pattern of cardiac cycles 50. A correlation analysis with the template cardiac cycle of all cardiac cycles that have not been previously grouped is performed, numeral 68. That is, each cardiac cycle not already assigned to a group (i.e., all of the cardiac cycles in the first iterative pass, all previously unassigned cardiac cycles in subsequent passes) is compared to the template cardiac cycle on a point-by-point basis. Any conventional correlation analysis may be utilized for this purpose. The preferred correlation utilizes a correlation calculation of the form $$\text{corr}(i, j) = \frac{c(i, j)}{\sqrt{c(i, i) c(j, j)}}$$

that is performed on a point-by-point basis between the template and the cardiac cycle under consideration at that moment. In this relation, c(i,j) is the covariance, given by semi-regularly occurring event. A second type of cardiac cycle 56 is an irregularly occurring, anomalous cardiac cycle.

The cardiac cycle 56 may be associated with an ailment of the heart, or be a naturally occurring but irregular feature of the heart. The present invention is not intended to make the determination of the cause and effect of heart irregularities and the like. Instead, the present invention is a tool by which the heart researcher or physician may gather cardiac cycle information and organize a large body of data into a comprehensible form. In this regard, it should be noted that in a real situation, the pattern 50 may extend for hours, with the individual cardiac cycles occurring at roughly one second intervals. There may be many types of regularly or semi-regularly occurring cardiac cycles such as 52. Thus, a vast body of data is generated. An irregular cardiac cycle such as the cardiac cycle 56 may occur once in this body of data, and must be identified and distinguished from the other features of the data. Further, it is important to understand the temporal and spatial relationships of all of the cardiac cycles with regard to the anatomy of the subject 28 and to each other.

FIG. 3 illustrates the process for analyzing the cardiac cycles. A biomagnetometer 22 like that of FIG. 1 is provided, numeral 60. (An ECG may be used instead of the biomagnetometer.) It is utilized to record a pattern of cardiac cycles like that of FIG. 2, numeral 62. The pattern is preferably digitized in the computer 40 and stored in data storage 42 for subsequent analysis, numeral 64.

The pattern of cardiac cycles is analyzed into a number of groups of similar cardiac cycles.

$$c(i,j) = \frac{1}{N} \sum_{i=0}^{N-j-1} x(i)y(i+j)$$

with c(i,i) and c(j,j) representing the autocorrelations of each beat at zero-lag and x(i) and y(i) representing the time series for the two beats being compared.

The result of such a correlation analysis is a numeral value for the degree of correlation of the cardiac cycle being evaluated with the template. That degree of correlation is compared with a preselected degree of correlation, provided as an input, numeral 70. If the degree of correlation is at least as good as the preselected degree, the cardiac cycle being evaluated is placed into the group associated with that particular template cardiac cycle, numeral 72. If the degree of correlation is less than the preselected degree of correlation, the cardiac cycle being evaluated is placed back into the ungrouped members of the pattern 50, for analysis on the next iteration.

This procedure is repeated for another group. For the next grouping, the template may again be chosen at random. A preferred approach, however, is to utilize as the template that cardiac cycle having the lowest degree of correlation with the template cardiac cycle of the prior group analysis. This selection helps to ensure that intermediate beats are assigned to the proper group by making the next template as different as possible from the prior template.

After a sufficient number of iterations through the grouping steps 66, 68, 70, and 72, the great number of cardiac cycles in the pattern 50 have been assigned to a much smaller number of groups. Experience in applying the present approach to heart measurements conducted during the reduction to practice of the invention has shown that a degree of correlation of about 0.9 for all groups results in about 1-4 groups being identified and filled. A lower preselected degree of correlation will result in a smaller number of groups, and a higher preselected degree of correlation will result in a larger number of groups. The researcher may analyze the stored pattern data using different preselected degrees of correlation to seek meaningful patterns of interest in a particular type of study. That is, a cardiologist preparing for surgery may require only a relatively low degree of correlation to identify features of interest. A heart researcher may require a much higher degree of correlation in order to study the fine structure of heart functions. A particular advantage of the present invention is that it permits adjustment of the preselected degree of correlation to suit the needs of each user of the system.

After the cardiac cycles of the pattern 50 have been classified into groups, those groups may be used in various ways. In a preferred application, shown in FIG. 3, a correlated average is performed on the cardiac cycles within each group on a point-by-point basis to smooth out measurement irregularities and system noise, producing a statistically smoothed, averaged cardiac cycle for that group, numeral 74. (A correlated average is performed by first time-aligning the cardiac cycles of the group and then averaging the time-aligned cardiac cycles on a point-by-point basis.) The averaged result reduces the effect of uncorrelated measurement noise in the processed signal. Such an average is meaningful, because the members of the group have already been associated using the correlation technique already discussed.

The result of this procedure is a catalog of one or more types of cardiac cycles of the subject. The members of the catalog of cardiac cycle types may be presented as averaged or not averaged data, as appropriate. The catalog of cardiac cycle types also includes the frequency of occurrence of the each type, so that each cardiac cycle type may be judged to be a regularly occurring cardiac cycle, a semi-regularly occurring cardiac cycle, or an irregularly occurring, anomalous cardiac cycle.

Heart researchers or doctors can use this information in their studies. For example, one class of cardiac cycle may be associated with the normal beating of the heart. Another class may be associated with normal irregular beats, which occur in most persons. Other classes may be associated with injury or certain types of illness. The raw data for the cardiac cycles remains available, so that once a particular class of cardiac cycles has been identified as of special interest, the nature of the cardiac cycle may be studied and the time-series relationship of the cardiac cycle to other cardiac cycles and groups may also be determined. These associations are outside the scope of the present invention, which is a tool for obtaining and making data on cardiac cycles available to researchers and doctors in a useful form for these further studies.

In a preferred application, the present approach is now being used to categorize changes in magnetocardiogram waveform morphology between normal, healthy subjects and subjects with documented episodes of ventricular tachycardia. One goal of this study is to determine if the subjects with ventricular tachycardia exhibit waveform patterns that can be used as a non-invasive marker of their risk for arrhythmias. Prior research has shown that if these patterns exist, their amplitude will be much smaller than the amplitude of the remainder of the cardiac cycle.

In order to discern these small signals, it is necessary to first reduce the uncorrelated measurement noise by averaging about 100 similar cardiac cycles for each patient. The present approach is used to screen a large number of cardiac cycles and identify this group of similar cycles for subsequent averaging.

Although a particular embodiment of the invention has been described in detail for purposes of illustration, various modifications may be made without departing from the spirit and scope of the invention. Accordingly, the invention is not to be limited except as by the appended claims.

What is claimed is:

1. Apparatus for measuring the physiology of the heart, comprising:
   means for detecting a series of cardiac cycles of a subject;
   means for storing the patterns of the series of cardiac cycles detected by the means for detecting;
   means for performing correlation analysis of cardiac cycles in the series of cardiac cycles; and
   means for classifying groupings of cardiac cycles, the means for classifying comprising
   means for identifying a first template cardiac cycle,
   means for forming a first selected group of cardiac cycles from among those of the series of cardiac cycles having at least a first preselected degree of correlation with the first template cardiac cycle, and leaving a first ungrouped group of cardiac cycles having a correlation less than the first preselected degree of correlation,
   means for selecting a second template cardiac cycle from the first ungrouped group of cardiac cycles, and
   means for forming a second group of cardiac cycles from among the first ungrouped group of cardiac cycles having at least a second preselected degree of correlation with the second template cardiac cycle, and leaving a second ungrouped group of cardiac cycles having a correlation less than the second preselected degree of correlation.

2. The apparatus of claim 1, wherein the means for detecting includes a biomagnetometer that detects the magnetic fields produced by cardiac cycles.

3. The apparatus of claim 1, wherein the means for classifying further includes
   means for selecting a further template cardiac cycle from among those not previously selected, and
   means for forming a further group of cardiac cycles from among the those not previously selected having at least a preselected degree of correlation with the further template cardiac cycle.

4. The apparatus of claim 1, further including
   means for averaging, on a point-by-point basis, all of the cardiac cycles in a group.

5. The apparatus of claim 1, wherein the means for selecting a second template includes means for selecting the cardiac cycle having a lowest degree of correlation with the first template.

6. Apparatus for measuring the physiology of the heart, comprising:
   biomagnetometer means for detecting magnetic fields produced by a beating heart of a subject;
   means for storing the patterns of a series of cardiac cycles detected by the biomagnetometer means;
   means for performing correlation analysis of cardiac cycles in the series of cardiac cycles; and
   means for classifying the series of cardiac cycles into a plurality of groups, the means for classifying including means for identifying each group, including
   means for identifying a group template cardiac cycle, and
   means for forming a group of cardiac cycles from among those of the series of cardiac cycles not previously classified into a group and having at least a preselected degree of correlation with the template cardiac cycle.

7. The apparatus of claim 6, wherein the apparatus further includes
   means for averaging, on a point-by-point basis, all of the cardiac cycles in a group.

8. The apparatus of claim 6, further including
   means for identifying a group containing an anomalous cardiac cycle.

9. The apparatus of claim 6, wherein each succeeding template cardiac cycle is selected as the remaining ungrouped cardiac cycle having the lowest degree of correlation with the last-selected template cardiac cycle.

10. A method for measuring the physiology of the heart, comprising the steps of:
    providing an apparatus that detects cardiac cycles of a subject;
    detecting magnetic signals corresponding to a time sequence of a plurality of cardiac cycles of a subject, utilizing the apparatus; and
    classifying the series of cardiac cycles into a number of groups according to the degree of correlation of each cardiac cycle with a template cardiac cycle for each group.

11. The method of claim 10, including the additional step, after the step of classifying, of
    associating the cardiac cycles of at least one group with a physical condition of the subject.

12. The method of claim 10, wherein the step of classifying includes the substeps of
    selecting a template cardiac cycle against which other previously ungrouped cardiac cycles are to be correlated;
    performing a correlation analysis of all previously ungrouped cardiac cycles with the template cardiac cycle; and
    associating with the template cardiac cycle all previously ungrouped cardiac cycles having at least a preselected degree of correlation therewith, to form a group.

13. The method of claim 12, including the further step of repeating the steps of selecting, performing, and associating until all cardiac cycles have been associated with a group.

14. The method of claim 13, wherein the template cardiac cycle for each succeeding group is that previously ungrouped cardiac cycle having the lowest degree of correlation with the previous template cardiac cycle.

15. The method of claim 12, further including a step, after the step of associating, of
    identifying a group containing an anomalous cardiac cycle.

16. The method of claim 12, further including a step, after the step of associating, of
    averaging, on a point-by-point basis, all of the cardiac cycles in a group.

17. The method of claim 10, wherein the apparatus is a biomagnetometer.

18. The method of claim 10, wherein the apparatus is an electrocardiograph.

* * * * *